(12) United States Patent
Lipowicz

(10) Patent No.: US 8,752,557 B2
(45) Date of Patent: Jun. 17, 2014

(54) AEROSOL GENERATOR

(71) Applicant: Philip Morris USA Inc., Richmond, VA (US)

(72) Inventor: Peter Lipowicz, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

(21) Appl. No.: 13/667,241

(22) Filed: Nov. 2, 2012

(65) Prior Publication Data

US 2013/0074854 A1 Mar. 28, 2013

Related U.S. Application Data

(63) Continuation of application No. 11/302,492, filed on Dec. 14, 2005, now Pat. No. 8,322,350.

(60) Provisional application No. 60/640,089, filed on Dec. 30, 2004.

(51) Int. Cl.
A24F 47/00 (2006.01)

(52) U.S. Cl.
USPC ........... 131/271; 131/273; 131/274; 131/335; 131/337

(58) Field of Classification Search
None
See application file for complete search history.

(56) References Cited

U.S. PATENT DOCUMENTS

| | | | |
|---|---|---|---|
| 4,281,671 A | 8/1981 | Bynre et al. |
| 4,284,089 A | 8/1981 | Ray |
| 4,765,348 A | 8/1988 | Honeycutt |
| 4,813,437 A | 3/1989 | Ray |
| 4,889,144 A | 12/1989 | Tateno et al. |
| 4,907,605 A | 3/1990 | Ray et al. |
| 4,920,989 A | 5/1990 | Rose et al. |
| 4,945,929 A | 8/1990 | Egilmex |
| 4,953,572 A | 9/1990 | Rose et al. |
| 5,074,320 A | 12/1991 | Jones, Jr. et al. |
| 5,087,424 A | 2/1992 | Liljewall |
| 5,167,242 A | 12/1992 | Turner et al. |
| 5,335,678 A | 8/1994 | Andersson |
| 5,400,808 A | 3/1995 | Turner et al. |
| 5,501,236 A | 3/1996 | Hill et al. |
| 5,564,442 A | 10/1996 | MacDonald et al. |
| 5,593,684 A | 1/1997 | Baker et al. |
| 5,656,255 A | 8/1997 | Jones |
| 5,721,257 A | 2/1998 | Baker et al. |
| 5,834,011 A | 11/1998 | Rose et al. |
| 5,893,371 A | 4/1999 | Rose et al. |
| 5,939,100 A | 8/1999 | Albrechtsen et al. |
| 5,952,378 A | 9/1999 | Stjernschantz et al. |
| 6,024,097 A | 2/2000 | Von Wielligh |
| 6,041,789 A | 3/2000 | Bankert et al. |
| 6,085,745 A | 7/2000 | Levander et al. |
| 6,098,632 A | 8/2000 | Turner et al. |
| 6,102,036 A | 8/2000 | Slutsky et al. |
| 6,129,936 A | 10/2000 | Gustafsson |
| 6,506,425 B2 | 1/2003 | Gustafsson |
| 8,322,350 B2 | 12/2012 | Lipowicz |

FOREIGN PATENT DOCUMENTS

| | | |
|---|---|---|
| GB | 2032244 A | 5/1980 |
| WO | WO 97/12639 | 4/1997 |
| WO | WO 2005/053444 A1 | 6/2005 |

OTHER PUBLICATIONS

Center for Drug Evaluations and Research; Application No. NDA-20-714, Medical Reviews, 1996.
Pfizer, Nicotrol Inhaler Excerpts, www.nicotrol.com/inhaler, 2003.
International Search Report dated Jun. 23, 2006 for PCT/IB2005/004054.
International Preliminary Report on Patentability dated Jul. 3, 2007 for PCT/IB2005/004054.

*Primary Examiner* — Michael J Felton
(74) *Attorney, Agent, or Firm* — Buchanan Ingersoll & Rooney PC

(57) ABSTRACT

An aerosol generator device for delivering an aerosol of a nicotine salt is provided. The aerosol generator comprises: (i) a mouth end; (ii) a first chamber containing a porous material wetted with liquid nicotine, (iii) a second chamber containing a porous material wetted with a solution of a volatile acid, (iv) a third chamber in fluid communication with the first and second chambers, leading to the mouth end, and (v) an outer housing defining a passageway for air through said device. A nicotine vapor can be produced by drawing air along the passageway and through the porous material wetted with liquid nicotine. An acid vapor can be produced by passing air along the passageway and through the porous material wetted with a solution of a volatile acid. Then, the nicotine vapor and the acid vapor can be admixed in the third chamber to form an aerosol of a nicotine salt, which can be drawn out through the mouth end.

9 Claims, No Drawings

AEROSOL GENERATOR

FIELD OF INVENTION

The invention relates generally to a nicotine aerosol generator and methods of manufacturing same, as well as methods for delivering an aerosol of a nicotine salt and methods for assisting a person to stop smoking and/or providing a substitute for tobacco smoking.

BACKGROUND

As an alternative to smoking cigarettes, certain products have been developed as tobacco-smoking alternatives or substitutes. Such products include, for example, nicotine-containing chewing gum, nicotine-containing nose drops, nicotine skin patches, lozenges, and nicotine sprays. For example, see U.S. Pat. Nos. 4,793,366; 4,813,437; 4,920,989; 4,945,929; 4,953,572; 5,656,255; 5,834,011; 5,893,371; and 6,024,097.

Often these tobacco-smoking alternatives or substitutes have certain drawbacks. For instance, these products may not sufficiently simulate the experience of smoking a cigarette. In particular, the nicotine levels produced are typically lower than those produced by tobacco smoking. Also, the absorption of nicotine into the bloodstream is slower than with conventional tobacco smoking. Moreover, these substitute methods sometimes have unpleasant side effects, including nausea, indigestion and throat or mouth irritation.

Accordingly, it is desirable to provide improved alternatives or substitutes for tobacco smoking and/or products for delivering nicotine as part of a program to assist smokers to discontinue smoking cigarettes.

SUMMARY

An aerosol generator for delivering an aerosol of a nicotine salt is provided. In an embodiment, the aerosol generator device for delivering an aerosol of a nicotine salt, comprises (i) a mouth end; (ii) a first chamber containing a porous material wetted with liquid nicotine; (iii) a second chamber containing a porous material wetted with a solution of a volatile acid; (iv) a third chamber in fluid communication with both the first and second chambers, and leading to the mouth end, and (v) an outer housing defining a passageway for air through said device. The outer housing preferably contains at least the first and second chamber, and may also contain the third or any additional chambers as well.

A nicotine vapor can be produced by passing or drawing air through the porous material wetted with liquid nicotine. An acid vapor can be produced by passing or drawing air through the porous material wetted with a solution of a volatile acid. The nicotine vapor and the acid vapor can be admixed in the third chamber to form an aerosol of a nicotine salt, which can be drawn out the mouth end.

The aerosol of the nicotine salt produced is about 0.1 to 10 microns in size, preferably about 0.1 to 3 microns in size.

In an embodiment, the volatile acid in the second chamber is selected from the group consisting of hydrochloric acid, phosphoric acid, acetic acid and sulphuric acid.

In another embodiment, the form of the liquid nicotine is (i) a racemic mixture, (ii) an unequal amount of the D and L isomers of nicotine, (iii) substantially the D isomer of nicotine or (iv) substantially the L isomer of nicotine. Preferably, the form of the nicotine is substantially the L isomer.

If desired, either the first chamber or the second chamber further comprise at least one additive selected from the group consisting of a viscosity agent, an antioxidant or a preservative. Optionally, the aerosol generator may further comprise a fourth chamber, wherein the fourth chamber contains at least one additive selected from the group consisting of water, alcohol and flavoring. In another embodiment, the aerosol generator may optionally further comprise in the mouth end, a sufficient amount of a basic compound to remove any excess acid vapor, for example, calcium carbonate can be used to remove acid vapor from the aerosol. Examples of flavoring that may be incorporated into the aerosol generator include menthol, for example.

In one embodiment, an aerosol generator contains a total of about 1-50 mg of nicotine, preferably about 1-20 mg of nicotine per device. For example, the aerosol generator can dispense about 0.5 to 20 mg of nicotine to the user, preferably about 0.5 to 10 mg of nicotine to the user. The aerosol generator can include a 10 mg nicotine capsule to deliver about 4 mg of nicotine to the user. In general, the aerosol generator delivers an inhalation volume of about 10 to 1000 cc per draw or puff, preferably an inhalation volume of about 35 to 350 cc per draw or puff. In certain embodiments, the person would use about 5-20 cartridges a day, but this number can vary depending upon the personal preference of the user.

In yet another embodiment, a method for assisting in the reduction of the desire of a subject to smoke tobacco and/or providing to a smoker a substitute for tobacco smoking is provided. Such methods comprise using an aerosol generator as described herein to deliver an aerosol of a nicotine salt to a subject.

DETAILED DESCRIPTION

The invention relates generally to an aerosol generator for delivering an aerosol of a nicotine salt.

In one embodiment, the aerosol generator comprises: (i) a mouth end; (ii) a first chamber containing a porous material wetted with liquid nicotine, (iii) a second chamber containing a porous material wetted with a solution of a volatile acid, and (iv) a third chamber in fluid communication with both the first and second chambers, and leading to the mouth end.

A nicotine vapor can be produced by passing air through the porous material wetted with liquid nicotine. The nicotine is vaporized as a result of its vapor pressure. An acid vapor can be produced by passing air through the porous material wetted with a solution of a volatile acid. Then, the nicotine vapor and the acid vapor can be contacted in the third chamber as the user draws them up through the device by inhaling from the mouth end.

While not wishing to be limited by theory, it is believed that contacting the two vapor-laden streams allows the nicotine to contact the acid in the vapor phase, causing an acid-base reaction between the basic nicotine molecule, and the acid to form a nicotine salt. The nicotine salt has low volatility, and forms an aerosol, which can be drawn out the mouth end.

Advantages of the aerosol device over other aerosol generators include the simplicity of design and operation, and the small aerosol particle size generated. Also, the aerosol generator as described herein advantageously does not require any excipients or aerosol carrier. In addition, the aerosol generator does not pose a fire risk, and also does not produce second-hand or sidestream smoke. Advantageously, the aerosol of the nicotine salt is delivered substantially free of tar, and also free of mainstream smoke.

The aerosol generator in one embodiment is in the shape of a tube with a mouth end. The mouth end may optionally contain a filter type material if desired. The user is able to draw air through the tube from the mouth end, such that the air is passed through both the first chamber and second chamber.

Optionally, in a preferred embodiment, the mouth end can further contain a suitable material to absorb any solid and/or excess acid vapor. Often a basic compound is used for this purpose, such as a carbonate. Preferably, calcium carbonate may be used for this purpose.

In an embodiment, the aerosol generator is in the shape of a tube, which is about 1-15 cm long and 5-10 mm in diameter. Preferably, the aerosol generator is about 7-8 cm long and about 7 mm in diameter. In one embodiment, the aerosol generator may be in the form of a double-barreled tube, with the third chamber at the mouth end of the tube.

In a preferred embodiment, the aerosol generator will have the appearance and be about the same size as a cigarette. In this regard, a regular cigarette is about 70 to 120 mm long, preferably about 85 mm, and the circumference is from about 15 mm to about 30 mm in circumference, preferably about 25 mm.

Nicotine is extracted from tobacco in the form of a water-soluble, alkaline, oily liquid. The chemical structure of nicotine is as follows:

3-(1-methylpyrrolidin-2-yl)pyridine
$C_{10}H_{14}N_2$
Mol. Wt.: 162.23
pKa1-7.84, pKa2 = 3.04 at 15° C.

As illustrated above, nicotine is a tertiary amine comprising a pyridine and a pyrrolidine ring. It is colorless to pale yellow in color, and turns brown on exposure to air or light. Nicotine is also a volatile, hygroscopic liquid. Accordingly, to extend the shelf life in a commercial embodiment, it may be desirable that the aerosol generator be wrapped in foil or a sealed packaging material, to minimize the exposure to air and light. Prior to use, the user can conveniently remove the packaging material.

The liquid nicotine used in the aerosol generator may be in the form of (i) a racemic mixture, (ii) an unequal amount of the D and L isomers, (iii) substantially the D isomer or (iv) substantially the L isomer. By "substantially" is meant that a specific enantiomer will contain less than 10%, e.g. less than 5% and advantageously less than 1%, e.g., less than 0.5% of its opposite enantiomer. Preferably, the L-isomer is used (which corresponds to the S-isomer when using the Cahn-Ingold-Prelog nomenclature system).

The term "liquid nicotine" includes both nicotine in the liquid or oil form, as well as nicotine in the form of a solution. In a preferred embodiment, a physiologically acceptable solution is used, for example, including but not limited to, water, saline or phosphate-buffered saline.

The nicotine is placed on a suitable porous material. Preferably, the porous material is inert. Examples of porous materials that may be used include, but are not limited to various fibers and polymer materials. The outer housing for the aerosol generator is constructed from a suitable material, such as a plastic or various suitable paper materials.

It is to be understood that the aerosol generated comprises a gaseous suspension of fine solids or liquid particles. The mass mean aerodynamic diameter (MMAD) of these particles is typically from about 0.1-10 microns. In contrast, a vapor is the gaseous state of a substance that is normally a liquid or solid under standard temperature and pressure. It is noted that a vapor in gaseous form is typically exposed to the mouth of the user, while an aerosol in particulate form can be exposed to the lungs of the user. Inhaling an aerosol also mimics the sensation of inhaling smoke from a standard cigarette better than a vapor.

Any suitable acid may be used in the second chamber. By "suitable acid," it is understood that the acid must be selected such that it is volatile enough to be admixed with the nicotine vapor, and such that it is strong enough to react with the nicotine. In addition, the acid should be selected such that it is physiologically acceptable. Examples of suitable acids include, but are not limited to, acetic acid and possibly hydrochloric acid, phosphoric acid, sulphuric acid, and mixtures thereof.

As mentioned above, the size of the aerosol particles is sufficient to simulate the sensation normally achieved by tobacco smoke. For example, the MMAD of the aerosol particles is typically between about 0.1-10 microns, preferably 0.1-3 microns.

In a further embodiment, the aerosol generator may also further comprise a fourth chamber, wherein the fourth chamber contains at least one additive selected from the group consisting of water, alcohol and flavoring. Any suitable flavoring agent may be used, such as but not limited to menthol.

The materials in each of the chambers may additionally contain suitable amounts of other additives such as, but not limited to standard viscosity agents (e.g., cellulose or substituted cellulose such as carboxymethyl cellulose, lanolin, beeswax, gum arabic, PEG), preservatives (e.g., benzoic acid) and/or antioxidants (e.g., ascorbic acid).

In yet another embodiment, a method for assisting a person to quit smoking is provided, which comprises delivering an aerosol of a nicotine salt, wherein the aerosol of the nicotine salt is of such particle size and quantity to provide comparable or reduced uptake of nicotine as compared to tobacco smoking. In an embodiment, suitable levels of nicotine may be used, for example, levels suitable for use in a method for assisting in the reduction of the desire of a subject to smoke tobacco and/or for providing to a smoker a substitute for tobacco smoking.

While the invention has been described with reference to preferred embodiments, it is to be understood that variations and modifications may be resorted to as will be apparent to those skilled in the art. Such variations and modifications are to be considered within the purview and scope of the invention as defined by the claims appended hereto.

All of the above-mentioned references are herein incorporated by reference in their entirety to the same extent as if each individual reference was specifically and individually indicated to be incorporated herein by reference in its entirety.

What is claimed is:

1. A method for assisting in the reduction of the desire of a subject to smoke tobacco or providing to a subject a substitute for tobacco smoking, which method comprises delivering to said subject an aerosol of a nicotine salt produced by the following steps:
   producing a nicotine vapor by passing air through a porous material wetted with liquid nicotine;
   producing an acid vapor by passing air through a porous material wetted with a solution of a volatile acid, and
   admixing the nicotine vapor and the acid vapor to form the aerosol of a nicotine salt, and
   contacting the aerosol with a basic compound in an amount effective to remove acid vapor in the aerosol.

2. A method of claim 1, where the nicotine aerosol is generated by an aerosol generator which delivers about 0.5 to 20 mg of nicotine.

3. A method of claim 2, where the aerosol generator delivers about 0.5 to 10 mg of total nicotine.

4. A method of claim 2, where the aerosol generator delivers an inhalation volume of about 10 to 1000 cc per puff or draw.

5. A method of claim 2, where the aerosol generator delivers an inhalation volume of about 35 to 350 cc per puff or draw.

6. A method of using an aerosol generator device for delivering an aerosol of a nicotine salt, comprising:

flowing or drawing air through an aerosol generator device comprising a mouth end; a first chamber containing a porous material wetted with liquid nicotine; a second chamber containing a porous material wetted with a solution of a volatile acid; a third chamber in fluid communication with the first and second chambers, and leading to the mouth end, and an outer housing defining a passageway for the air through said device, producing nicotine vapor by passing at least some of the air through the porous material wetted with liquid nicotine, producing acid vapor by passing at least some of the air through the porous material wetted with a solution of a volatile acid, and admixing the nicotine vapor and the acid vapor in the third chamber to form an aerosol of a nicotine salt, contacting the aerosol with a basic compound in an amount effective to remove acid vapor in the aerosol, which is drawn out the mouth end.

7. A method of producing an aerosol of nicotine salts, comprising:

producing a nicotine vapor by passing air through a porous material wetted with liquid nicotine;

producing an acid vapor by passing air through a porous material wetted with a solution of a volatile acid, and admixing the nicotine vapor and the acid vapor to form the aerosol of a nicotine salt, and contacting the aerosol with a basic compound in an amount effective to remove acid vapor in the aerosol.

8. A method of producing an aerosol of nicotine salts, comprising:

producing a nicotine vapor by passing air through a porous material wetted with liquid nicotine;

producing an acid vapor by passing air through a porous material wetted with a solution of a volatile acid, admixing the nicotine vapor and the acid vapor to form the aerosol of a nicotine salt, and contacting the aerosol with a basic compound in an amount effective to remove acid vapor in the aerosol.

9. A method of claim 8, wherein the basic compound is calcium carbonate.

* * * * *